(12) United States Patent
Hansen et al.

(10) Patent No.: US 6,692,472 B2
(45) Date of Patent: Feb. 17, 2004

(54) INJECTION DEVICE, A PREASSEMBLED DOSE SETTING AND INJECTION MECHANISM FOR AN INJECTION DEVICE, AND A METHOD OF ASSEMBLING AN INJECTION DEVICE

(75) Inventors: Steffen Hansen, Hillerød (DK); Thomas Dedenroth Miller, København (DK)

(73) Assignee: Novo Nordisk A/S, Bagsvaerd (DK)

( * ) Notice: Subject to any disclaimer, the term of this patent is extended or adjusted under 35 U.S.C. 154(b) by 63 days.

(21) Appl. No.: 09/846,798

(22) Filed: May 1, 2001

(65) Prior Publication Data

US 2002/0007154 A1 Jan. 17, 2002

Related U.S. Application Data

(60) Provisional application No. 60/204,678, filed on May 17, 2000.

(30) Foreign Application Priority Data

May 4, 2000 (DK) ........................................ 2000 00739

(51) Int. Cl.[7] ................................................ A61M 5/00
(52) U.S. Cl. ...................................... 604/211; 604/210
(58) Field of Search ................................ 604/211, 224, 604/207, 208, 209, 210

(56) References Cited

U.S. PATENT DOCUMENTS

| | | | |
|---|---|---|---|
| 5,514,097 A | 5/1996 | Knauer | |
| 5,697,916 A | * 12/1997 | Schraga | 604/207 |
| 5,928,201 A | * 7/1999 | Poulsen et al. | 604/208 |
| 5,947,934 A | * 9/1999 | Hansen et al. | 604/211 |
| 6,074,372 A | 6/2000 | Hansen | |
| 6,248,090 B1 | * 6/2001 | Jensen et al. | 604/207 |

FOREIGN PATENT DOCUMENTS

| | | |
|---|---|---|
| WO | WO 98/10812 | 3/1998 |
| WO | WO 98/56436 | 12/1998 |

* cited by examiner

*Primary Examiner*—Gregory L. Huson
*Assistant Examiner*—Khoa Huynh
(74) *Attorney, Agent, or Firm*—Reza Green, Esq.; Richard W. Bork, Esq.; Marc A. Begon, Esq.

(57) ABSTRACT

An injection device made up from a housing, a dose setting and injection mechanism, a dose setting member and an injection button is described. The dose setting and injection mechanism is made as a preassembled unit insertable into the housing. Both the dose setting member and the injection button is thereafter connected to the preassembled dose setting and injection mechanism inside the boundaries of the housing, while being accessible for a user from outside the housing. The same preassembled dose setting and injection mechanism can fit into a large variety of different houses making production of different variants of an injection device somewhat easier.

10 Claims, 5 Drawing Sheets

INJECTION DEVICE, A PREASSEMBLED DOSE SETTING AND INJECTION MECHANISM FOR AN INJECTION DEVICE, AND A METHOD OF ASSEMBLING AN INJECTION DEVICE

This application claims the benefit of provisional application No. 60/204,678 filed May 17, 2000.

THE TECHNICAL FIELD OF THE INVENTION

The invention relates to injection devices of the kind comprising a housing accommodating an cartridge, a dose setting and injection mechanism, a dose-setting member coupled to the dose setting and injection mechanism, and an injection button coupled to the dose setting and injection mechanism and by which a piston rod drive can be activated for advancing the piston rod forward to press out a set dose through a conduit connected to the cartridge.

The invention furthermore relates to a preassembled dose setting and injection mechanism for an injection device.

Finally the invention relates to a method of assembling an injection device.

DESCRIPTION OF THE RELATED ART

A prior art injection device of this kind is shown in WO 98/56436, which injection device is also shown in FIG. 1 of this application. This device consists of three basic parts; a dose setting and injection mechanism, a dose-setting member and an injection button. The dose setting and injection mechanism contains a piston rod 1 and a piston rod drive comprising gear wheels 2 and 3, a coupling ring 4, and a driver 5. The coupling ring 4 and the driver 5 are connected through a unidirectional coupling. The dose-setting element 6 has a carrier 7 and a finger grip 8. The injection button 9 works a not shown gearwheel placed at the hub of the coupling ring 4.

In injection devices of this type the dose setting and injection mechanism is made as an integrated part of the housing. The outer shape of the housing has to facilitate the appearance of the dose setting and injection mechanism, and the housing is moulded with a number of protrusions supporting the various elements of the dose setting and injection mechanism.

DESCRIPTION OF THE INVENTION

If for some reason an injection device with a different outer design is needed, it is necessary to reconstruct the entire dose setting and injection mechanism in order to fit it into the new redesigned housing. This takes a substantial amount of time, both to the reconstruction of the entire device, but also to get the proper approvals from the authorities. Therefore many manufactures of injection devices are very reluctance to market new injection devices, designed in accordance with the trends in the world of fashion.

Although a new type of injection devices are approved by the authorities prior to the marketing, there always persists a small risk of malfunction due to an erroneous construction of the dose setting and injection mechanism. Another safety disadvantage is that the function of the dose setting and injection mechanism cannot be tested once the injection device is assembled, while it is impossible to move the piston rod backwards once the injection device is assembled.

It is an object of the present invention to provide an injection device where the outer design of the housing can be altered without having to change the dose setting and injection mechanism. Further, it is an object to provide an injection device, which can be new in design but having a save and well-proven dose setting and injection mechanism, thereby minimizing the risk of malfunction. Finally it is an object of the present invention to provide an injection device where the function of the dose setting and injection device can be properly tested before the injection device is completely assembled.

This is obtained by an injection device having a housing accommodating an cartridge containing medicine sufficient for a number of dosed injections, which doses are injected by advancing a piston forward inside said cartridge, comprising:

A dose setting and injection mechanism comprising a piston rod abutting said piston and a piston rod drive for driving said piston rod, A dose-setting member coupled to said dose setting and injection mechanism for setting up a dose, and An injection button coupled to said dose setting and injection mechanism and by which said piston rod drive can be activated for advancing said piston rod and said piston forward to press out a set dose through a conduit connected to said cartridge, Which injection device according to the invention is characterized in that said dose setting mechanism is a preassembled unit insertable into said housing to form a complete assembly, and that said dose-setting member and said injection button, both being accessible for the user from outside said housing, is connected to said preassembled dose setting and injection mechanism inside the boundaries of said housing.

By making the dose setting and injection mechanism as a preassembled unit, this unit is independent of the housing, and if a new injection device with a new outer design is called for it is fairly simple to redesign the housing and then insert the standardized dose setting and injection mechanism. From a manufacturing point of view production of a large variety of injection devices each carrying a different design is made very simple by using a preassembled dose setting and injection mechanism. But from a safety point of view it is certainly a great safety issue to be able to manufacture injection devices with a new outer design, but still containing the well proven standardized dose and injection mechanism of an earlier device.

It is also a particular advantage that the preassembled dose setting and injection mechanism permits a testing of the function of the mechanism before the complete assembly is done.

When, as disclosed in claim 2, the dose-setting member is provided with a number of carriers, which carriers is received in depressions in said preassembled dose setting and injection mechanism, it is in a very handy way ensured that the dose-setting member interfaces the preassembled dose setting and injection mechanism. The carriers could be provided with click-pawls, which would lock the dose-setting member to the preassembled dose setting and injection device in a inseparable way.

When, as disclosed in claim 3, the injection button is provided with a toothed rack, which toothed rack is received in a slot in said preassembled dose setting and injection mechanism, it is ensured that the longitudinal movement of the injection button is transferred to a rotational movement of the coupling ring. The injection button could be provided with a protrusion, which fits into a longitudinal track in the housing, thereby locking the injection button to the housing.

It is also an object of the present invention to provide a preassembled dose setting and injection mechanism, which can be fitted into a large variety of different housings.

This is obtained by a preassembled dose setting and injection mechanism for an injection device according to the invention, which preassembled dose setting and injection mechanism is characterized in that said preassembled dose setting and injection mechanism comprises:

a coupling ring driven by said injection button, a driver driving the piston rod through a suitable gearing, and a unidirectional coupling connecting the coupling ring and the driver in a unidirectional manner.

By making the dose setting and injection mechanism as a single preassembled unit it will be possible to recycle the injection device. The recycled device can be disassembled, and the preassembled dose setting and injection mechanism can be reused after the piston rod has been moved backward to its original position. The other parts of the injection device can off cause be recycled in the same manor. The various parts can either be recycled by using the same part again as described, or more likely, the various parts can be sorted into the different types of plastic and then granulated for recycling.

Finally it is an object of the invention to provide a method of assembling an injection device in a way, which is both easy and inexpensive.

This is obtained by a method of assembling an injection device according to the invention, which method is characterized in comprising the steps of:

a) Preassembling the dose setting and injection mechanism to provide a preassembled unit, b) Placing the preassembled unit in the housing and connecting said preassembled unit to said housing, c) Connecting the dose-setting member to said preassembled unit inside the boundaries of said housing, and d) Connecting the injection button to said preassembled unit inside the boundaries of said housing.

This method makes production somewhat easier since one production line constantly can produce and assembly the standardized dose setting and injection mechanism, while other production lines again can manufacture housings of various designs. The preassembled dose setting and injection mechanism can then be placed inside the various houses.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENTS

Figure 1:
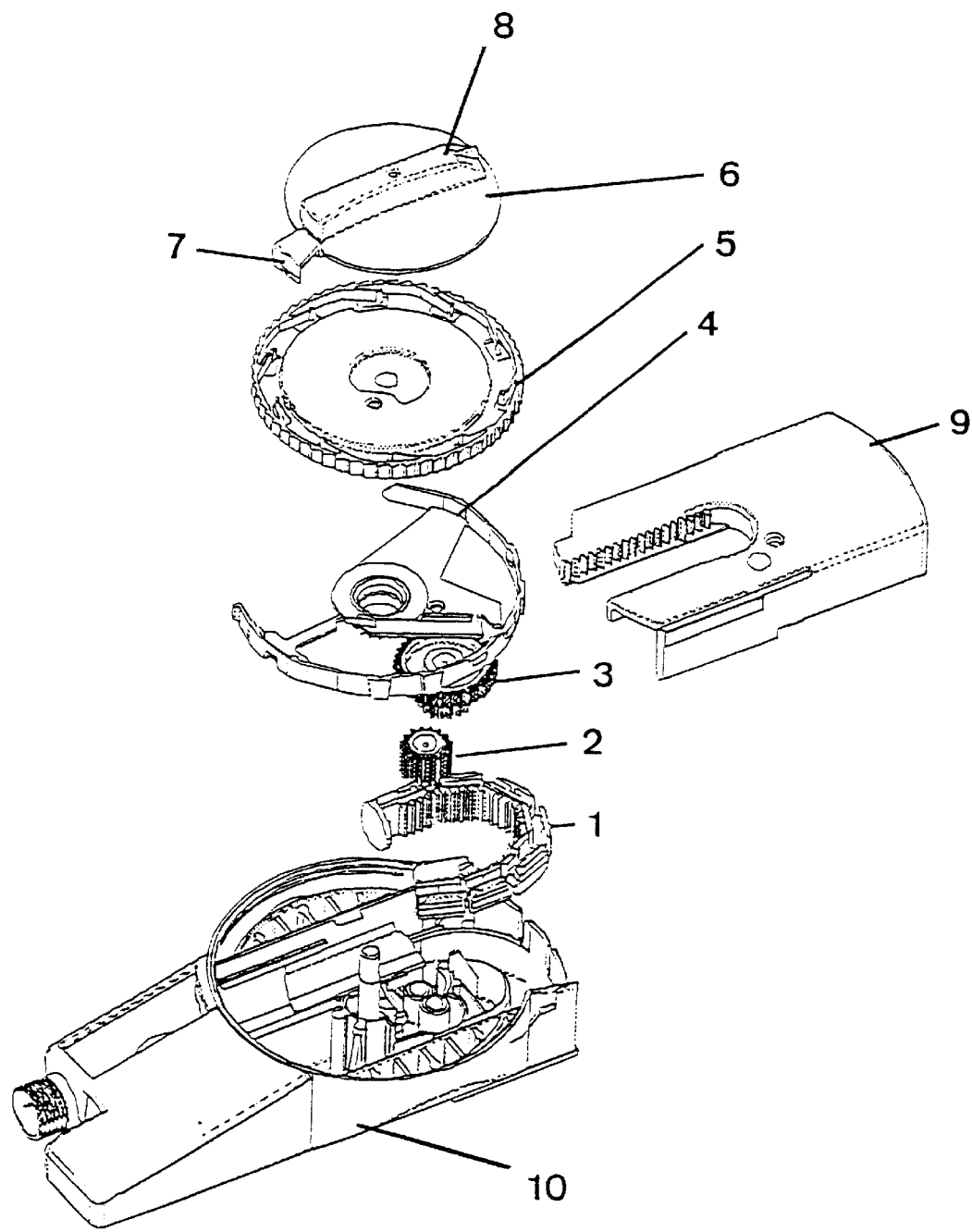
FIG. 1 Shows an exploded view of the prior art injection device.

FIG. 1 shows an injection device according to the preamble of claim 1. This injection device contains three basic parts; a dose setting and injection mechanism being fully built into the housing 10, a dose-setting member 6 and an injection button 9. The dose setting and injection mechanism contains a piston rod 1 and a piston rod drive comprising gear wheels 2 and 3, a coupling ring 4, and a driver 5. The dose-setting member 6 for setting up a dose is integral with the carrier 7 and the finger grip 8. The injection button 9 works a not shown gearwheel placed at the hub of the coupling ring 4. When setting up a dose by rotating the dose-setting member 6, the coupling ring 4 is rotated due to the carrier 7 placed on the dose-setting member 6. This rotation will lift the injection button 9 away from the device. Pressing back the injection button 9 will cause the coupling ring 4 to rotate, since this ring through a unidirectional coupling is connected to the driver 5, this driver 5 will also rotate. A not shown gear wheel placed on the hub of the driver 5 engages the first gear wheel 3 which again engages the second gear wheel 2 and advances the piston rod 1. A more detailed description of this prior art injection device is given in WO 98/56436.

Figure 2:
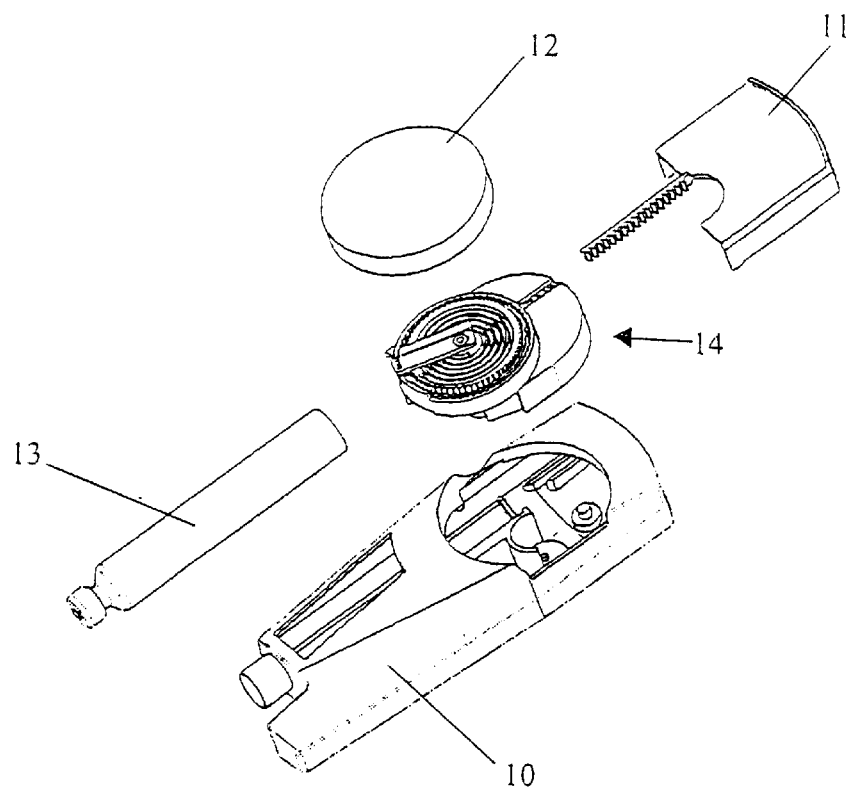
FIG. 2 Shows an exploded top view of the injection device according to the invention.

An injection device according to the invention is shown in FIG. 2. This device is made from a housing 10 containing a cartridge 13 containing medicine sufficient for a number of dosed injections. Inserted into the housing 10 is a preassembled dose setting and injection mechanism 14, which inside the boundaries of the housing 10 is connected to the injection button 11 and to the dose-setting member 12.

Figure 3:
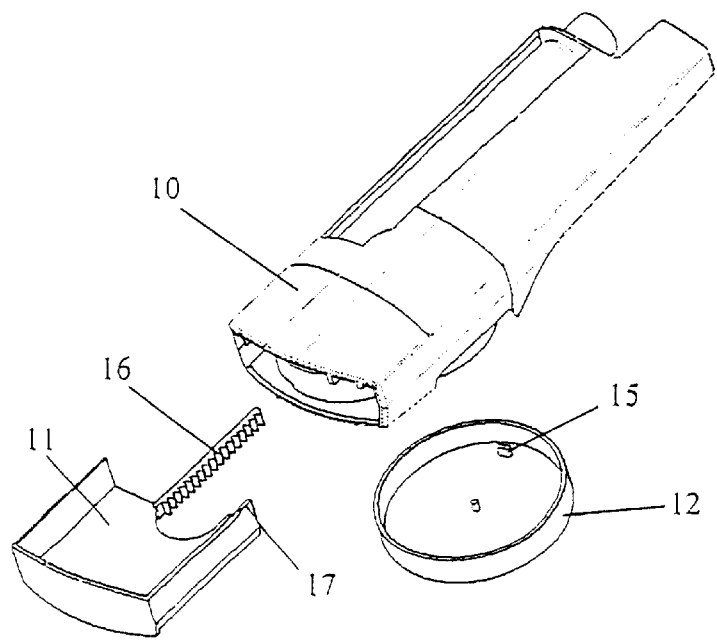
FIG. 3 Shows an exploded bottom view of the injection device according to the invention.

As shown in FIG. 3 the dose-setting member 12 has on its backside a carrier 15, which is connected to the preassembled dose setting and injection mechanism 14 as will be described later. Although only one carrier 15 is shown there could off cause be more than one carrier 15 if so wanted. The injection button 11 is connected to the preassembled dose setting and injection mechanism 14 through a toothed rack 16. The injection button 11 is preferably provided with a protrusion 17, which protrusion 17 is guided in a not shown track in the housing 10, which track has a not shown stop-pawl, which prevents the injection button 11 from being disconnected from the housing 10. When manufacturing the housing, this could be done by moulding the housing in two parts, which two parts then could be glued together, or otherwise connected.

Figure 4:
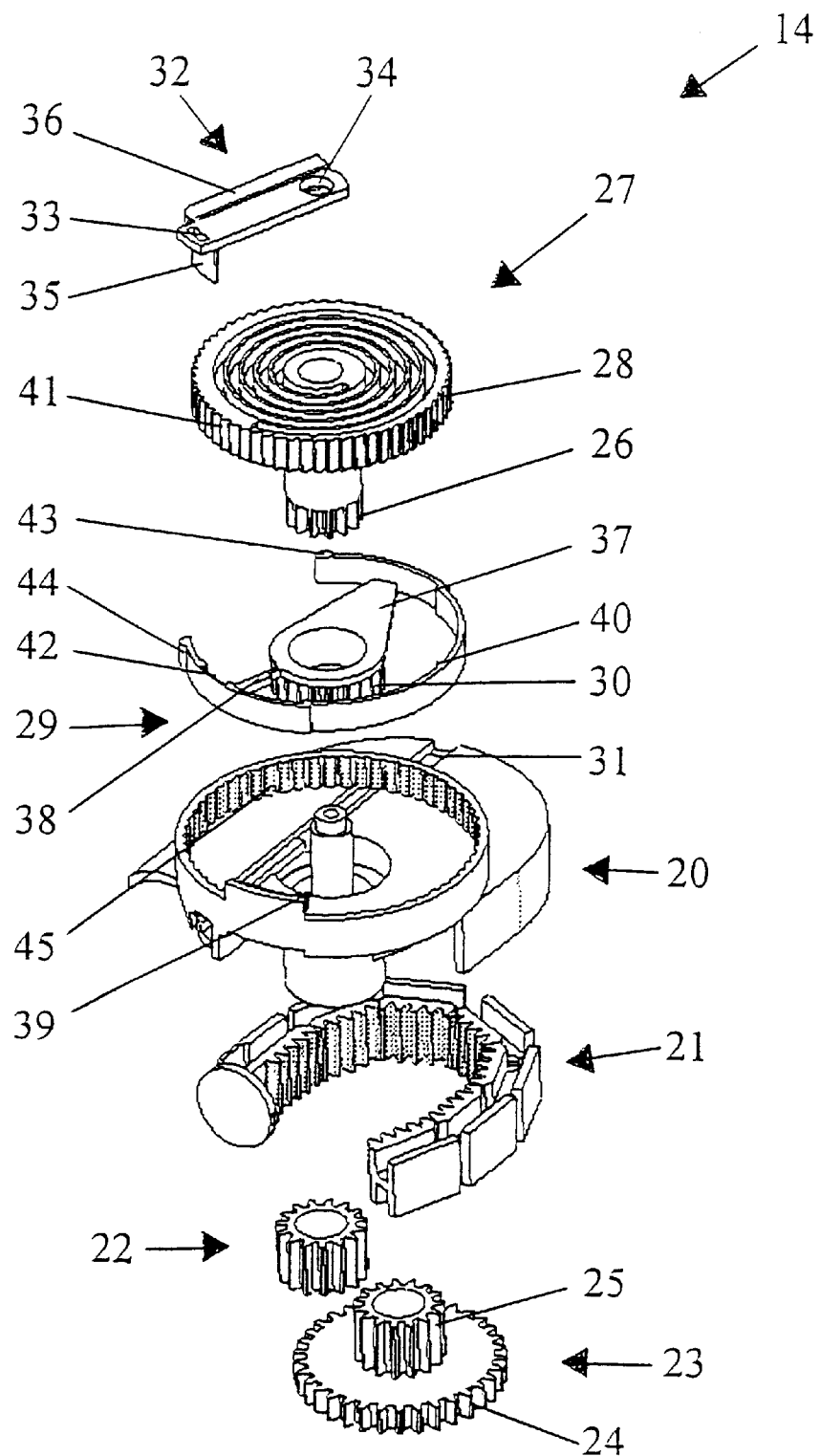
FIG. 4 Shows an exploded view of the preassembled dose setting and injection mechanism.
Figure 5:
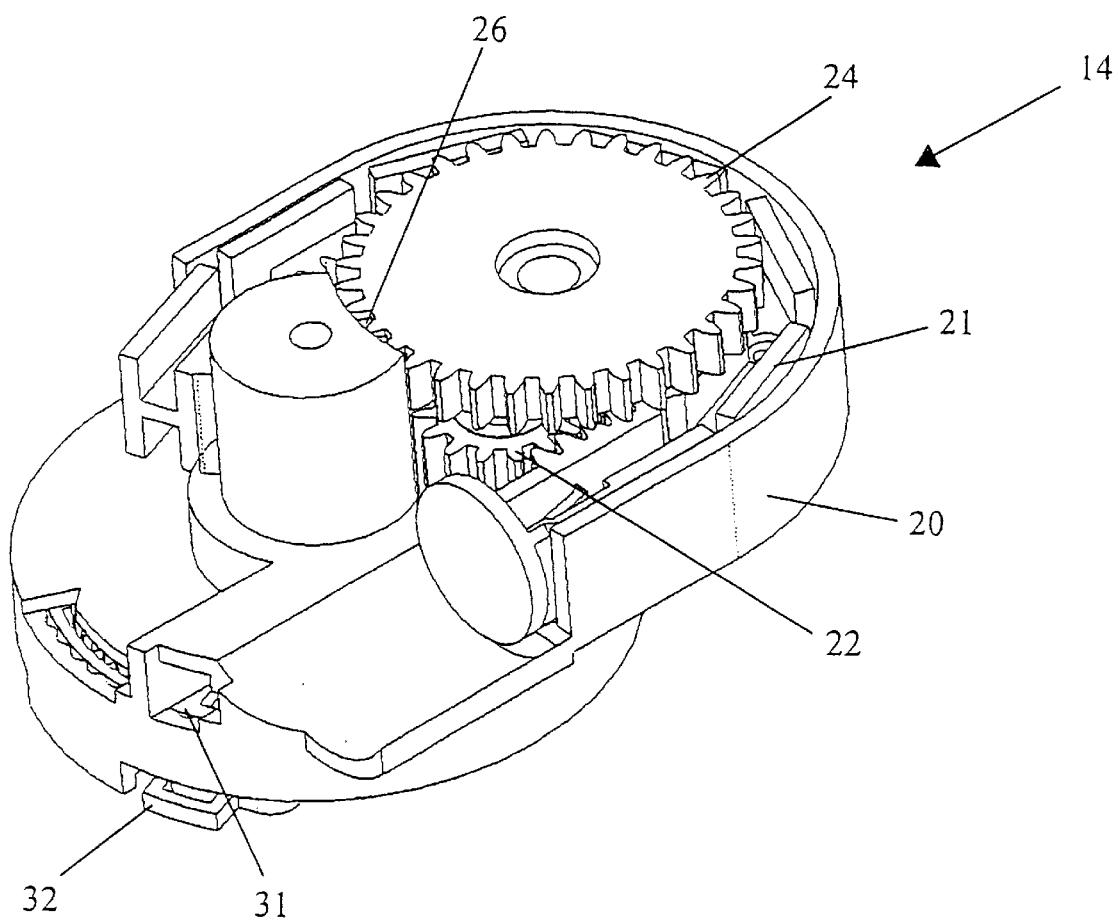
FIG. 5 Shows a schematically bottom view of the preassembled dose setting and injection mechanism.
Figure 6:
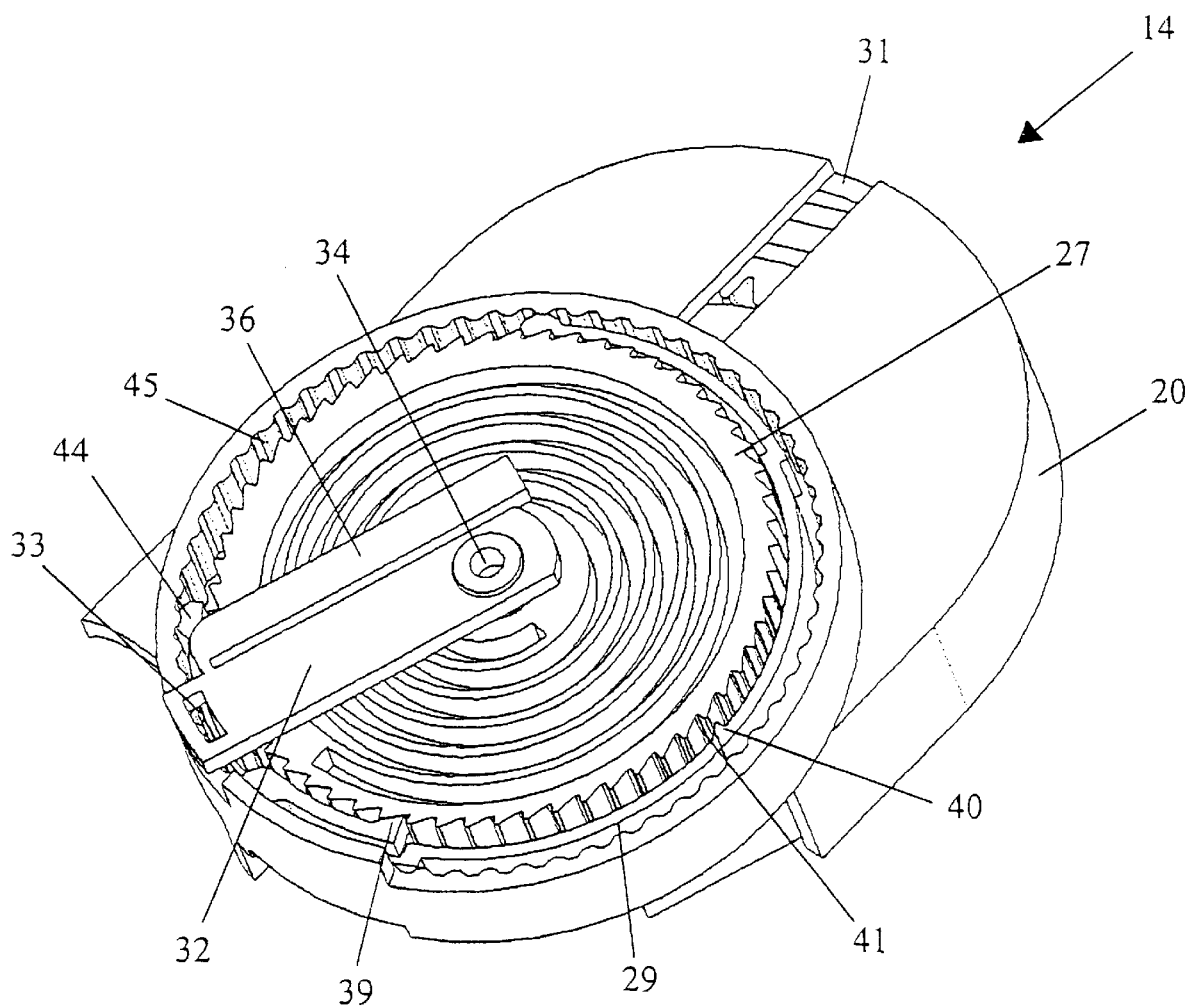
FIG. 6 Shows a schematically top view of the preassembled dose setting and injection mechanism.

Referring now to FIG. 4 to 6, the preassembled dose setting and injection mechanism 14 is made up from a rod guiding part 20 in which a flexible piston rod 21 is guided. The rod guiding part 20 has a slot 31 and an inwardly pointing protrusion 39. The flexible rod 21 is being driven by a first gear wheel 22, which again is being driven by the hub-wheel 25 of the second gear wheel 23. The second gear wheel 23 is made up from an outer gear wheel 24, which is integral with a hub-wheel 25. The outer gearwheel 24 is driven by the hub-wheel 26 on the driver 27. This driver 27 also has an outer gear wheel 28, which is located inside the coupling ring 29 and in unidirectional contact with the coupling ring 29. The coupling ring 29 is provided with a hub-wheel 30, which hub-wheel 30 is driven by the toothed rack 16, guided in a slot 31, of the injection button 11 when the injection device is being operated.

The entering part of the slot 31 formed in the rod guiding part 20 need not be formed as an open track-like slot 31 as shown in FIG. 6, but can easily be made as a slot 31 solely accessible from the periphery of the rod guiding part 20 i.e. similar to the exit part of the slot 31 shown in FIG. 5.

The hub-wheel 30 of the coupling ring 29 is connected to the coupling ring 29 through a rigid part 37 and a flexible part 38. The coupling ring 29 has on its inside a number of barbs 40, which barbs 40 interconnects with the barbs 41 of the outer gear-wheel 28 of the driver 27.

The barbs 41 at the outer gear wheel 28 of the driver 27 are by a protrusion 39 located on the rod guiding part 20 prevented from rotation in one direction. The direction in which the driver can move freely is the direction by which the piston rod 21 is moved forward in the cartridge 13.

An arm 32 is at the centre 34 connected to the centre of the rod guiding part 20. On the other end, the arm 32 is equipped with a cam 35 interacting with a notch 42 provided at the rim of the coupling ring 29, thereby locking the arm 32 to the coupling ring 29. The arm 32 also has a depression 33 into which to the carrier 15 on the backside of the dose-setting member 12 is fitted. A second arm 36 is situated parallel to the first arm 32 and is connected thereto through a flexible beam. The second arm 36 has on its backside a not shown cam, situated near the centre 34. This cam is movable locked in the spiral shaped track of the driver 27. In this way the number of rotations the driver 27 can perform relatively to the second arm 32 and the rod guiding part 20 is limited, and the total length of the track is adapted to the total amount of medicine in the cartridge 13 thereby ensuring that a dose larger than the amount of medicine remaining in the cartridge 13 cannot be set.

When operating the injection device the dose is set by turning the dose-setting member 12, which is connected to the arm 32. Due to the connection between the cam 35 on the arm 32 and the notch 42 on the coupling ring 29, the coupling ring 29 is rotated to. Since the hub 30 of the coupling ring 29 is connected to the toothed rack 16 of the injection button 11, this button 11 is lifted away from the injection device. Due to the protrusion 39 interfering with the barbs 41, the driver 27 is prevented from rotating, while the barbs 40 rides over the barbs 41 on the driver 27. This at the same times makes an audible sound.

If a set dose is regretted the dose-setting member 12 is rotated in the opposite direction. Due to the flexible part 38 of the coupling ring 29, the coupling ring 29 expands outward, allowing the barbs 40 to slide over the barbs 41 of the driver 27. Hence the driver 27 is not affected by this backward rotation of coupling ring 29.

The bulging ends 43, 44 provided at the coupling ring 29 rides over the barbs 45 situated on the inside of the rod guiding part 20 and keeps the coupling ring 39 stretched at all times such that the bulging ends 40 interconnects with the barbs 41 of the driver 27

When delivering the set dose, the injection button 11 is pressed home. The toothed rack 16 of the injection button 11 works the hub-wheel 30 of the coupling ring 29. This rotates the coupling ring 29, where the barbs 40 force the outer gear wheel 28 of the driver 27 and the hub-wheel 26 to rotate. The hub-wheel 26 rotates the outer gear wheel 24 of the second gear wheel 23 being integral with the hub-wheel 25, which rotates the first gear wheel 22. Rotation of the first gear-wheel 22 causes the piston rod 21 to advance inside the cartridge 13, thereby expelling the set dose of medicine though the not shown needle connected to the distal end of the cartridge 13.

When manufacturing an injection device according to the invention, the dose setting and injection mechanism 14 is first assembled into a preassembled unit 14. Then the preassembled unit 14 is placed in the housing 10 and connected to the housing through suitable means. Pressing the carrier 15 into the depression 33 on the arm 32 of the preassembled unit 14 connects the dose-setting member 12 to the preassembled unit 14. Finally the injection button 11 is connected to the preassembled unit 14 by placing the toothed rack 16 of the injection button 11 into the slot 31 of the preassembled unit 14.

Assembling the preassembled unit 14 can be done in one production line, while other production lines can do the final assembling of the various injection devices using the same preassembled unit 14.

Some preferred embodiments have been shown in the foregoing, but it should be stressed that the invention is not limited to these, but may be embodied in other ways within the subject matter defined in the following claims. The principles described could e.g. easily be adapted to a pencil shaped injection device without derogating from the scope of the claims.

What is claimed is:

1. A dose setting and injecting mechanism for use with injection devices having housings, the mechanism comprising:
   a. piston rod;
   b. a piston rod drive means for driving the piston rod, the piston rod drive means being operatively coupled to the piston rod;
   c. a dose setting means for setting prescribed; and
   d. an injection means for activating the piston rod drive means to drive the piston;
   wherein: the piston rod, piston rod drive means, the dose setting means, and the injection means are operably connected to form a complete operating module that does not require structural assistance from an injection device's housing to function.

2. The dose setting and injection mechanism of claim 1, further comprising a means for connecting the mechanism to an injection button and a means for connecting the mechanism to a dose setting member.

3. The dose setting and injection mechanism of claim 2, wherein the dose setting member and injection button are located on the outside on an injection device housing and wherein the connecting means are located internally within the injection device housing.

4. An injection device comprising:
   a. a housing having an interior and exterior;
   b. a cartridge having a movable piston;
   c. an injection button for allowing a user to inject a dose, the injection button having at least a portion that is accessible from the exterior of the housing;
   d. a dose setting member mounted to the housing and being accessible from the exterior of the housing
   e. a pre-assembled dose setting and injecting mechanism comprising:
      i. a piston rod;
      ii. a piston rod drive means that is operatively coupled to the piston rod;
      iii. a dose setting means for setting a prescribed dose and for controlling the drive of the piston rod drive means;
      iv. an injection means for activating the piston rod drive means;
      wherein: the individual parts comprising the dose setting and injection mechanism, including parts i–iv, are pre-assembled as a functional module that does not require the housing for structure or operation; and f. a means for securing the dose setting and injecting mechanism in the housing and operably coupling the mechanism to the injection button and dose setting member.

5. A method for assembling an injection device having a housing, a dose setting member exterior to the housing and an injection button exterior to the housing, the method comprising the steps of:

pre-assembling a dose setting and injection mechanism as a complete operable module that does not require housing from an injection device for structure;

inserting the pre-assembled dose setting and injection mechanism into the housing;

connecting the dose setting member to the pre-assembled mechanism; and connecting the injection button to the pre-assembled mechanism.

6. The method of claim 5, further comprising testing the pre-assembled mechanism prior to inserting it in the housing.

7. A complete testable dose setting and injecting mechanism for use with injection devices having housings, the mechanism comprising:

a. piston rod;

b. a piston rod drive means for driving the piston rod, the piston rod drive means being operatively coupled to the piston rod;

c. a dose setting means for setting prescribed; and d. an injection means for activating the piston rod drive means to drive the piston;

wherein: the piston rod, piston rod drive means, the dose setting means, and the injection means are operably connected to form a complete operating testable module that is testable apart from and prior to being inserted into an injection device housing.

8. A method for manufacturing an injection device comprising:

a. constructing an injection device housing having an injection button mounted therein, the injection button being accessible on the exterior of the housing;

b. manufacturing and preassemblying a dose setting and injection mechanism that are testable apart from the device housing; and c. inserting the dose setting and injection mechanism into the housing, whereby the dose setting and injection mechanism is operably coupled to the injection button.

9. The method of claim 8, wherein after step (b) but prior to step (c), the dose setting and injection mechanism is tested.

10. An injection device comprising:

a housing;

an injection button;

a selectively insertable and removable dose setting and injection mechanism that is operable and capable of being tested apart from the housing.

* * * * *